US012603153B2

(12) United States Patent
Simpson

(10) Patent No.: US 12,603,153 B2
(45) Date of Patent: Apr. 14, 2026

(54) DE NOVO GENERATION OF HIGH DIVERSITY PROTEINS IN SILICO WITH SELECTIVE AFFINITY AND CROSS-REACTIVITY MINIMIZATION

(71) Applicant: Thaumachron LLC, Rapid City, SD (US)

(72) Inventor: Andrew Simpson, Summerset, SD (US)

(73) Assignee: THAUMACHRON LLC, Rapid City, SD (US)

( * ) Notice: Subject to any disclaimer, the term of this patent is extended or adjusted under 35 U.S.C. 154(b) by 1241 days.

(21) Appl. No.: 17/396,197

(22) Filed: Aug. 6, 2021

(65) Prior Publication Data

US 2022/0093214 A1 Mar. 24, 2022

Related U.S. Application Data

(60) Provisional application No. 63/064,724, filed on Aug. 12, 2020.

(51) Int. Cl.
G16B 35/00 (2019.01)

(52) U.S. Cl.
CPC .................................... G16B 35/00 (2019.02)

(58) Field of Classification Search
CPC ......... G16B 35/00; G16B 15/30; G16H 20/10
See application file for complete search history.

(56) References Cited

U.S. PATENT DOCUMENTS 7,783,428 B2 * 8/2010 Gustafsson ............ G16B 40/20
702/19

OTHER PUBLICATIONS

Surendra S Negi, Werner Braun, Cross-React: a new structural bioinformatics method for predicting allergen cross-reactivity, Bioinformatics, vol. 33, Issue 7, Apr. 2017, pp. 1014-1020, https://doi.org/10.1093/bioinformatics/btw767 (Year: 2017).*
Tileli Amimeur, Jeremy M. Shaver, Randal R. Ketchem, J. Alex Taylor, Rutilio H. Clark, Josh Smith, Danielle Van Citters, Christine C. Siska, Pauline Smidt, Megan Sprague, Bruce A. Kerwin, Dean Pettit. bioRxiv 2020.04.12.024844; doi: https://doi.org/10.1101/2020.04.12.024844 (Year: 2020).*
Han, Y., Kim, D. Deep convolutional neural networks for pan-specific peptide-MHC class I binding prediction. BMC Bioinformatics 18, 585 (2017). https://doi.org/10.1186/s12859-017-1997-x (Year: 2017).*
Raphael R. Eguchi, Namrata Anand, Christian A. Choe, Po-Ssu Huang. IG-VAE: Generative Modeling of Immunoglobulin Proteins by Direct 3D Coordinate Generation. bioRxiv 2020.08.07.242347; doi: https://doi.org/10.1101/2020.08.07.242347 (Year: 2020).*
Jespersen MC, Mahajan S, Peters B, Nielsen M, Marcatili P. Antibody Specific B-Cell Epitope Predictions: Leveraging Information From Antibody-Antigen Protein Complexes. Front Immunol. Feb. 26, 2019;10:298. doi: 10.3389/fimmu.2019.00298. (Year: 2019).*

(Continued)

*Primary Examiner* — Karlheinz R. Skowronek
*Assistant Examiner* — Diana P Sanford
(74) *Attorney, Agent, or Firm* — Kutak Rock LLP; Brian L. Main; Ryan S. Hinderliter

(57) ABSTRACT

This disclosure relates to a platform for de novo in silico generation of high diversity protein complexes, namely antibodies and TCRs, with selective affinity and cross-reactivity minimization given the antigen complex's sequences and additional conditional information.

17 Claims, 6 Drawing Sheets

(56)             References Cited

OTHER PUBLICATIONS

John-William Sidhom, H. Benjamin Larman, Petra Ross-MacDonald, Megan Wind-Rotolo, Drew M. Pardoll, Alexander S. Baras. DeepTCR: a deep learning framework for understanding T-cell receptor sequence signatures within complex T-cell repertoires. bioRxiv 464107; doi: https://doi.org/10.1101/464107 (Year: 2019).*

Davidsen K, Olson BJ, DeWitt WS 3rd, Feng J, Harkins E, Bradley P, Matsen FA 4th. Deep generative models for T cell receptor protein sequences. Elife. Sep. 5, 2019;8:e46935. doi: 10.7554/eLife.46935. (Year: 2019).*

Dunbar J, Krawczyk K, Leem J, Marks C, Nowak J, Regep C, Georges G, Kelm S, Popovic B, Deane CM. SAbPred: a structure-based antibody prediction server. Nucleic Acids Res. Jul. 8, 2016;44(W1):W474-8. doi: 10.1093/nar/gkw361. Epub Apr. 29, 2016. (Year: 2016).*

Tan, C., Noviski, M., Huizar, J., & Zikherman, J. (2019). Self-reactivity on a spectrum: A sliding scale of peripheral B cell tolerance. Immunological reviews, 292(1), 37-60. https://doi.org/10.1111/imr.12818 (Year: 2019).*

Amimeur T, Shaver JM, Ketchem RR, et al. Designing Feature-Controlled Humanoid Antibody Discovery Libraries Using Generative Adversarial Networks. bioRxiv 2020.04.12.024844; DOI: https://doi.org/10.1101/2020.04.12.024844. (Year: 2020).*

* cited by examiner

DE NOVO GENERATION OF HIGH DIVERSITY PROTEINS IN SILICO WITH SELECTIVE AFFINITY AND CROSS-REACTIVITY MINIMIZATION

CROSS-REFERENCE TO RELATED APPLICATIONS

This application claims priority pursuant to 35 U.S.C. § 119(e) to U.S. Provisional Patent Application Ser. No. 63/064,724, filed Aug. 12, 2020, the entire disclosure of which is incorporated by reference.

FIELD OF THE INVENTION

This disclosure relates to the field of in silico protein development of high diversity proteins such as antibodies and T-cell receptors.

BACKGROUND OF THE INVENTION

Two important protein complexes of the adaptive immune response are antibodies and T-cell Receptors (TCRs). Both of these are protein complexes that use recombination to produce an enormous number of potential complexes. In the case of antibodies VDJ recombination is used and in the case of TCRs, VJ recombination. Human TCRs are estimated to have a diversity between $10^{15}$ and $10^{20}$ possible unique TCR sequences. Human antibodies are estimated to have a diversity of more than $10^{16}$ possible unique antibody sequences. This enormous repertoire of potential adaptive immune protein complexes allows the immune system to mount a response to essentially any novel threat. Antibodies work by binding to the 3D structure of an antigen whereas TCRs recognize peptide fragments loaded into the major histocompatibility complex (MHC). For example, a virus in interstitial fluid can be inactivated by antibodies and infected cells eliminated with TCRs that recognize viral peptide fragments.

Antibodies are "Y" shaped proteins that consist of a heavy and a light chain. The two chains are connected with a disulfide bond. The area of both chains of the antibody that binds to antigens for antibodies is known as the Fab (antigen-binding fragment) region. The Fab region consists of a variable region that contains a set of complementarity-determining regions (CDRs) that make up a paratope, the location on the antibody interacting with the epitope. Human antibodies consist of five isotypes that are different in the Fragment crystallizable region (Fc) of an antibody. Additionally, some isotypes have subclasses or subtypes that modulate the immune response. Allelic differences in individuals lead to different allotypes of antibodies.

TCRs consist of two chains either the more common α/β or the less common γ/δ variety. TCRs recognize fragments of an antigen processed by cells and displayed in MHC. Unlike antibodies, TCRs have low affinity towards antigen peptides and are degenerate in that many TCRs can recognize the same antigen and one TCR can recognize multiple antigens. For cancer immunotherapy treatments, this degeneracy is a major, potentially deadly, safety concern. In some cases, allelic difference between individuals may present peptides that would be recognized by a TCR used for cancer immunotherapy.

Both antibodies and TCRs are randomly created through recombination. This randomness has the potential to create self-reacting antibodies or TCRs. The immune system has a mechanism of negative selection known as central tolerance. Self-reacting antibodies are eliminated in the bone marrow and TCRs in the thymus.

Antibodies are a critical component of modern pharmacology allowing the ability to target specific antigens. Uses include treatment for many autoimmune disorders such as multiple sclerosis and for cancer immunotherapy such as checkpoint blockade, where mechanisms of peripheral tolerance are dampened. TCRs are also important in cancer immunotherapy allowing selective targeting of tumor specific antigens. One approach is to fuse the variable region of an antibody to TCR signaling components to create Chimeric antigen receptor T-cells (CAR T-cells) that has shown great promise in multiple types of cancers.

The timeline for creating a new biologic drug like antibodies is many years between identification and safety trials. Off target effects of antibodies or TCRs have potentially deadly consequences. Even research grade antibodies can take many months to go from an antigen to antibody production, and are not guaranteed to produce useful results. These timelines do not allow for rapid developments of treatments for new viruses or truly personalized cancer immunotherapy treatments. For some areas such as anti-venoms, polyclonal animal serums are used instead of fully humanized antibodies, which can potentially have serious safety concerns.

Other groups have attempted in silico antibody and to a lesser extent TCR design and development. Most of these rely on using x-ray crystal structures which are expensive and time consuming to create, if possible, or by using homology of related proteins. These are tools for research and not suitable for use in rapid development of treatments whether that is new monoclonal antibodies for rapid deployment to treat a new infectious disease or personalized cancer immunotherapy directed against tumor specific antigens unique to an individual. These tools also do not have the ability of negative self-selection or the ability to selectively control affinity.

In order to generate in silico antibodies, an epitope is needed for an antigen protein complex. In the case of linear epitopes, existing tools can predict with reasonable accuracy where antibodies could bind. For most real world situations, a 3D structure of the antigen complex is required. Epitopes can cross over multiple protein chains of an antigen complex. If an existing or closely related 3D structure is not available, current methods cannot predict likely epitopes for an antigen complex.

A unified platform for end-to-end de novo generation of high diversity proteins in silico would be well suited for the challenges of safety, time, and data availability of 3D structures that are involved in creating novel treatments.

BRIEF SUMMARY OF THE INVENTION

This disclosure is related to a web-based platform for de novo generation of high diversity protein complexes, namely, but not limited to, antibodies and TCRs, with selective affinity and cross-reactivity minimization in silico given only an antigen complex's sequences. The disclosed platform can generate these high diversity protein complexes nearly instantly. The generative models used may produce many different protein complexes that fit the given criteria. For additional safety, an exhaustive search for self-reactivity can be performed.

A user can upload an antigen complex's sequence(s) and select options relevant to the desired high diversity protein complex to be generated. The platform then outputs, but is not limited to, a high diversity protein complex, distance matrices (primarily distances between α-carbons in a square matrix), angle information (primarily φ and ψ dihedral angles of peptide bonds in protein chains), surface mesh representation (either a 3D mesh or flattened 2D mesh with labeled amino acid data), affinity, and epitope (if applicable). This information is used to reconstruct the three-dimensional structure of the generated protein complex. Additionally, distance matrices and angle information can be generated for the antigen complex and returned to the user along with the reconstructed three-dimensional antigen complex.

In the case of antibodies, additional options include, but are not limited to, species, isotype, subtype, and allotype. The user also has the option to explicitly set an epitope for an antigen along with affinity. If the affinity value is not set, the user can select the option of generating an affinity close to what naturally occurs with the antigen based on related antigens or select the option to maximize affinity. By default, antibodies are generated to minimize cross-reactivity for a given species. Some experiments may want to explore cross-reactivity, so the option to maximize cross-reactivity is given, but only for users that explicitly request the option.

In the case of antibody research, a user may want to have multiple epitopes generated for a given antigen complex. A user may select an option to only generate epitopes given an antigen complex's sequence(s) in order to generate an antibody for a specific biologically plausible epitope.

In the case of TCRs, additional user options include, but are not limited to, species, type (αβ, γδ), MHC class, and MHC/HLA allele combination. TCRs have relatively low affinity towards MHC complexes. By default, the affinity of the TCR to the antigen loaded MHC complex is automatically generated. Users can also set specific affinity values or allow for maximization or minimization of affinity.

Cross-reactivity is a major safety concern. By default, the generative models minimize cross-reactivity acting as an in silico version of central tolerance. The generated protein complexes are not guaranteed to be free of cross-reactivity. In order to improve the safety profile of the generated protein complexes, an exhaustive search of self-antigens can be performed. The user can either select a species or upload a genome or specific allelic differences. In the case of TCRs, self-antigens are generated using a specific MHC/HLA combination either provided or parsed from the uploaded genomic information.

After the sequences for the protein complexes are generated, the user may select an option to be sent directly to an oligonucleotide synthesizer to begin the process of protein creation or cell lines through various commercially available methods.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

Figure 1:
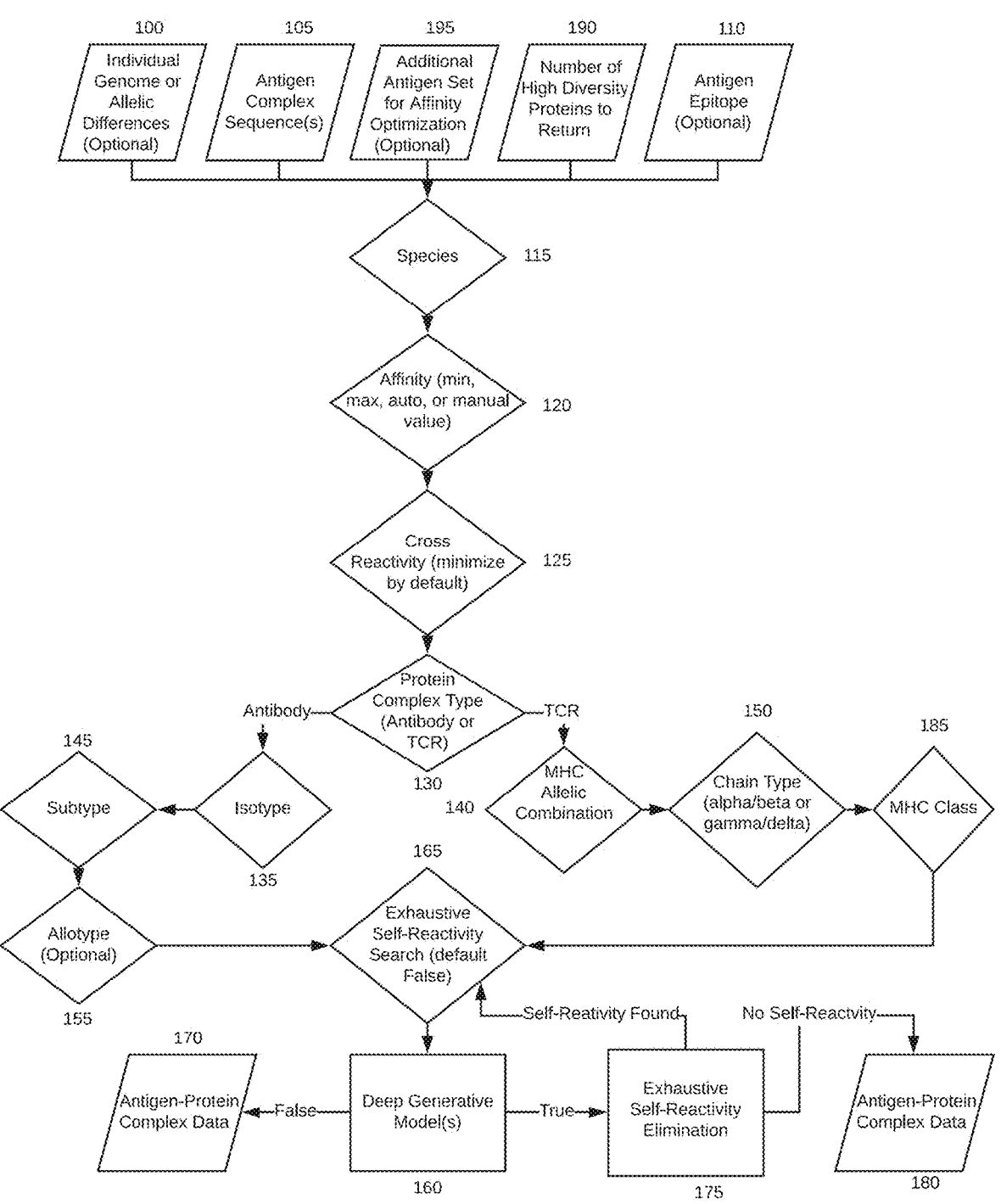
FIG. 1 Flow chart of user input to generate de novo protein complexes in silico, FIG. 2 Flow chart of antibody epitope generation.

This disclosure relates to a web-based platform for end-to-end de novo generation of high diversity proteins in silico, namely, but not limited to, antibodies and TCRs, with selective affinity and cross-reactivity minimization given only an antigen complex's sequence(s). FIG. 1 gives an overview of the process. A user is presented with a form to collect pertinent conditional information to generate the desired high diversity protein complexes. Users of this platform upload an antigen complex's sequence(s) 105 and select the type of high diversity protein complex to generate 130. Common between high diversity protein complexes is affinity value 120, cross-reactivity 125, the number of complexes returned 190, an additional set of antigen data for affinity optimization 195 (described later in FIG. 4 480), and an exhaustive self-reactivity search option 175. Affinity values may be set to a specific value, set to minimize, set to maximize, or set to allow an affinity value to be automatically set 120. In some cases, such as cancer immunotherapy, it is advantageous to target multiple antigens. A user also has an option to upload a set of antigen complex sequences and have results for all members of the set be generated 105.

One embodiment is the use of an individual's allelic variants from parsing a genome, exome, or a set of allelic differences. These allelic variants are used instead of the generic species alleles as seen in operation 100 in FIG. 1. The individual allelic differences can be used to develop personalized treatments such as, but not limited to, cancer immunotherapy. This operation parses uploaded genomic information using standard bioinformatics techniques and compares it to the generic species genome. Allelic differences replace generic species alleles for use in an exhaustive cross reactivity search 175. Additionally, allotypes and MHC/HLA allelic variants are automatically extracted for use in antibody and TCR generation.

In the case of TCRs, additional user options include, but are not limited to, species 115, type (αβ, γδ) 150, MHC class 185, and MHC/HLA allele combination 140. TCRs have relatively low affinity towards MHC complexes. By default, the affinity of the TCRs to the antigen loaded MHC complex is automatically generated 120. Research users can also set specific affinity values or allow for maximization or minimization of affinity.

Figure 2:
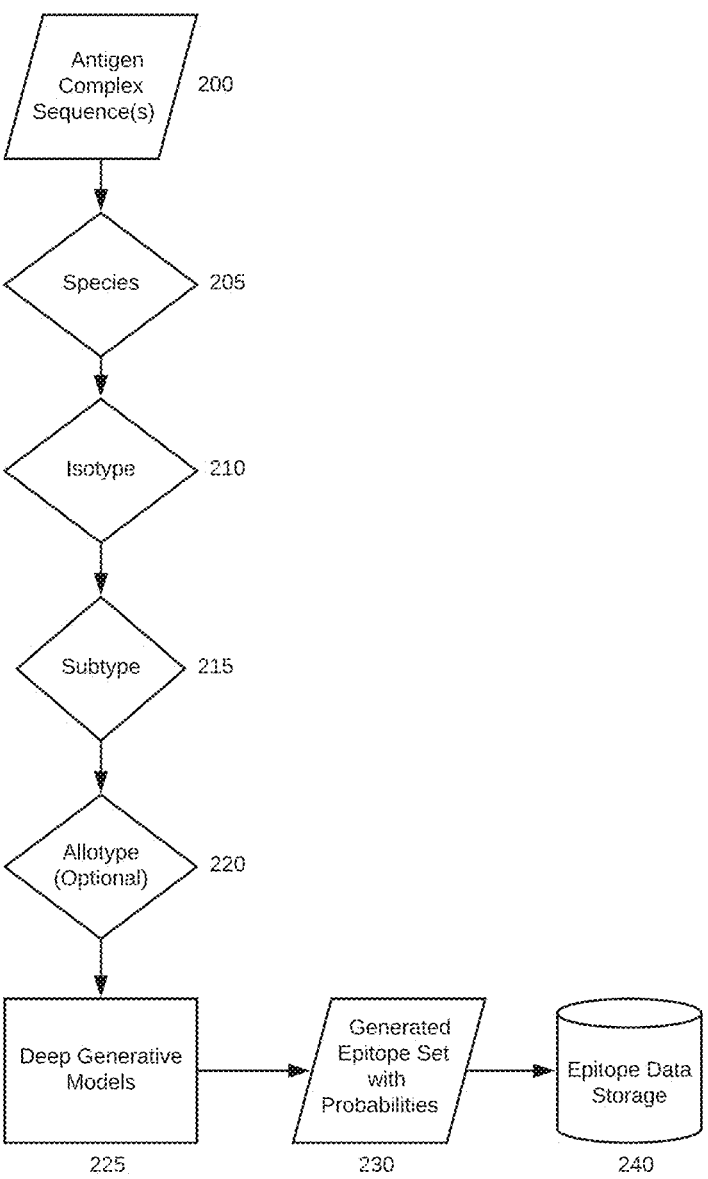

In the case of antibodies, additional options include, but are not limited to, species 115, isotype 135, subtype 145, and allotype 155. The user also has the option to have an epitope generated or explicitly set an epitope for the antigen complex, which can be generated separately using an antigen complex's sequence information as seen in FIG. 2. If the affinity value is not set, the user can select the option of generating an affinity close to what naturally occurs with the antigen based on related antigens or select the option to maximize affinity 120. By default, antibodies are generated to minimize cross-reactivity for a given species. Some experiments may want to explore cross-reactivity, so the option to maximize cross-reactivity is given but only for users that explicitly request this option 125.

Figure 4:
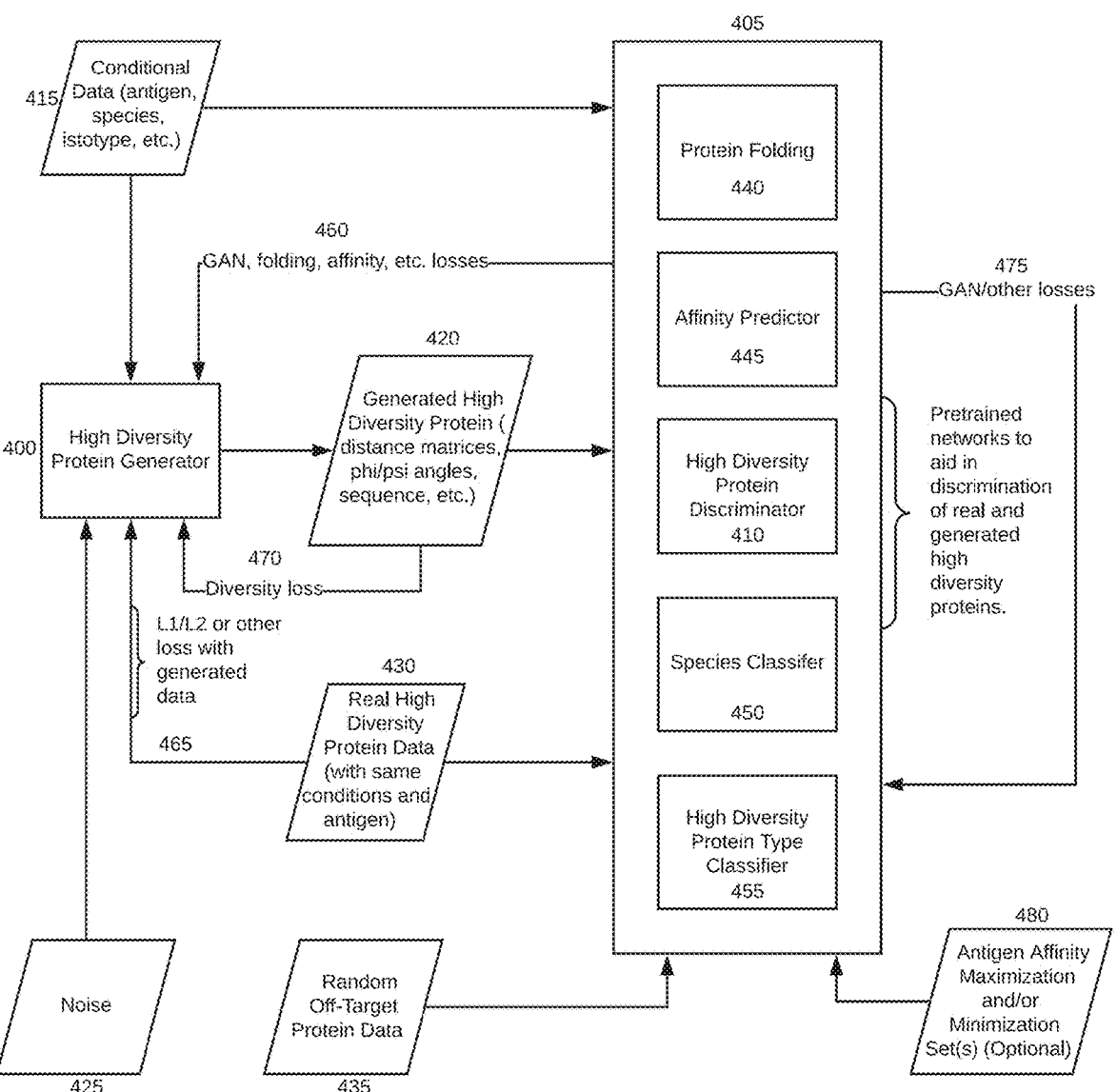
FIG. 4 Flow chart of generative model core architecture and training process.

The deep generative models, namely generative adversarial networks (GANs), used to create high diversity proteins are trained using a variety of pre-trained or partially pre-trained deep neural network modules as seen, but not limited to, named modules in FIG. 4. The primary generative model 400 takes as input conditional information 415 such as the antigen complex sequence and structure information, high diversity protein type, and other options mentioned in FIG. 1 along with noise 425, usually sampled from a multidimensional Gaussian distribution. The use of noise allows the generator network to produce non-deterministic output given conditional data and, through training of the generator and discriminator, allows sampling of the distribution of high diversity proteins that match the conditional information. In the case of TCRs, the allelic MHC differences are provided along with likely peptide epitopes from a separate trained network or other method. The discriminator 405 uses the same conditional data 415 in order to assess if the given input is either a generated 420 or a real 430 high diversity protein complex. The goal of the discriminator with pre-trained models 405 and the core discriminator 410 is to maximize the ability to tell the difference between real and generated data 475 whereas one of the generator's goals is to minimize the ability of the discriminator 405 and 410 to tell the difference between real and generated data 460. Loss functions from these additional neural networks are used to augment the GAN loss (460 for the generator and 475 for the discriminator) as shown in operation 460. The protein folding module 440 helps the generator to produce plausible 3D structural data. The affinity module 445 predicts the high diversity protein-antigen complex's affinity and is used to update the generator to match the expected affinity. The affinity module 445 also predicts the affinity of high diversity protein-random antigen complexes 435 for the generator to minimize. In certain applications, a user may want to maximize cross-reactivity. In this case, the loss is altered to maximize affinity 460 for random self-antigen complexes 435, or a user may maximize an uploaded set of antigen complexes 480 while still minimizing self-antigen complexes that are not in the uploaded set. Similarly, the species 450 and type module 455 aid in the training of the generative models to make sure the produced data matches the conditional information, such as human IgA. Additional features include, but are not limited to, a diversity loss 470 to increase the number of unique high diversity proteins produced and loss or loss functions related to a real high diversity protein meeting the same conditional information as the generated high diversity protein 465. The deep generative models and neural network modules are trained using a variety of publicly available data such as from Protein Data Bank (PDB) and the Immune Epitope Database (IEDB) with additional proprietary data such as, but not limited to, antibody/TCR affinity mutation data and off-target binding. The deep generative models model an underlying and unknown distribution of all high diversity protein complexes that would match the conditional information such as antigen complex sequence data, species, etc. that can be sampled from. The generative models are designed in such a way as to perform high quality protein folding, epitope generation, selective antigen affinity, and cross-reactivity minimization.

Figure 5:
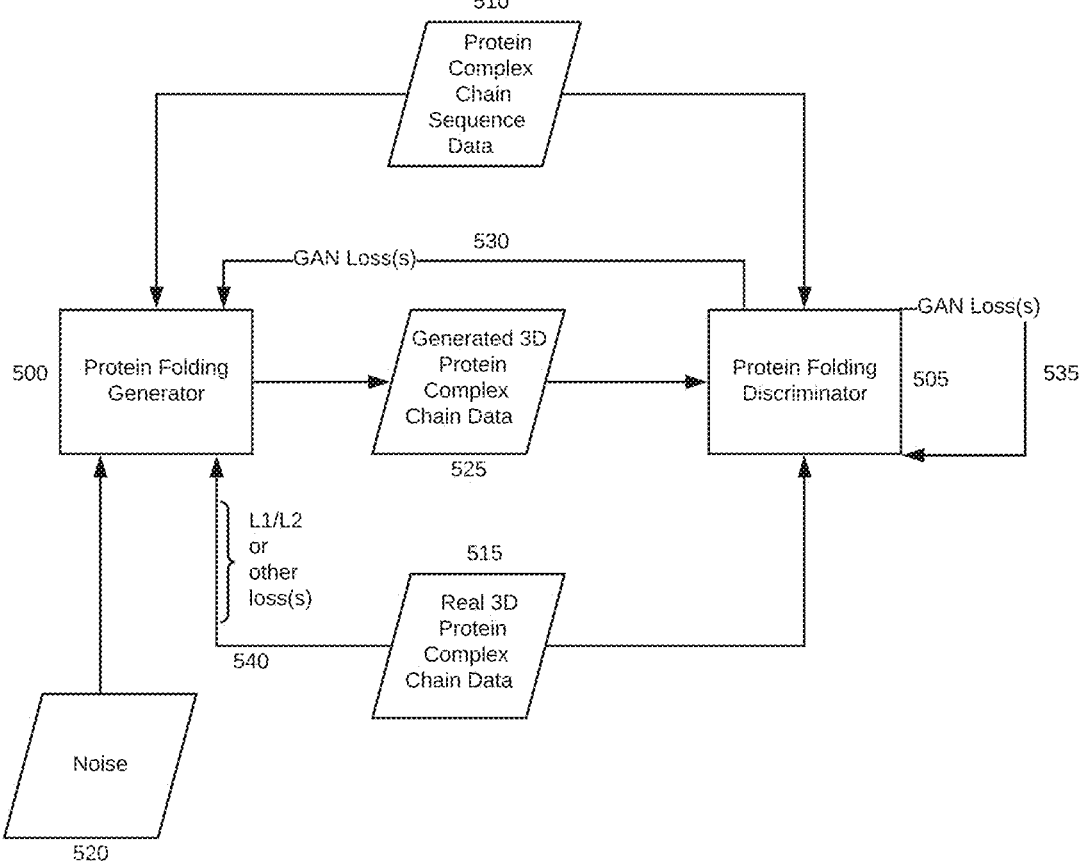
FIG. 5 Flow chart of protein folding model core architecture and training process.

Generally, only sequence data of an antigen is available due to cost and complexity. In order to make use of structural information for epitope generation in FIG. 2 and high diversity protein complex generation FIG. 4, structural information needs to be provided. In order to provide the necessary structural data, a high-performance protein folding deep generative model is used. Most proteins fold and crystallize in a consistent manner, but many proteins have multiple crystallization forms or other inconsistencies as can be seen in PDB data. Additionally, conformal changes are common in protein-protein and protein-ligand interactions that limit a purely supervised machine learning approach. A GAN architecture overcomes the difficulties of multiple 3D structures for protein chains. An overview of the protein folding GAN architecture can be seen in FIG. 5. Generated data includes, but is not limited to, distance matrices, phi psi angle information, and surface mesh representation. Training of this deep generative model uses amino acid embedding vectors using a continuous bag of words (CBOW) or skip-gram method commonly used in natural language tasks. Other information such as amino acid chemical properties may be included in the embedding vectors. Ligands may be represented using graphs and incorporated using geometric deep learning approaches. Since protein-protein interactions rely primarily on surface interactions, the use of the surface mesh representation allows for higher quality predictions from the affinity module 445. The "colors" of the protein surface mesh are the previously mentioned amino acid embedding vectors. Before training, protein surface meshes are constructed using standard computational geometry techniques such as alpha shape and flattened with techniques such as angle based flattening. Using a nearest neighbor or other approach each triangle in the mesh can be given a "color" from the embedding of the nearest amino acid on the protein's surface. The training of the protein folding generator 500 takes as input one or more protein complex chain sequence data 510 as conditional information and noise 520. The protein folding discriminator takes as input one or more protein complex chain sequences 510 as conditional information and either generated 3D protein complex chain data 525 or real 3D protein complex chain data 515. The goal of the discriminator is to maximize the ability to discern the difference between real and generated data using a GAN loss or other losses 535. The goal of the generator is to minimize the discriminators ability to discern real and generated data by using a GAN loss or other losses 530. The generated data is also compared to real expected data with the same sequences using an L1, L2 or other losses 540 to update the generator. In cases with multiple conformations this loss is relaxed in areas of heterogeneity in the 3D structures. The trained discriminator module 505 and/or the trained protein folding generator can be used for part of the discriminator in the high diversity protein GAN FIG. 4 module 440 in order to help the high diversity protein generator to produce plausible 3D structures. After a user uploads the pertinent information in FIG. 1 or FIG. 2, the uploaded antigen complex sequence data is given to the protein folding generator to produce conditional structural information for the high diversity protein GAN (FIG. 4) and epitope generator (FIG. 2 225).

One of the most important issues with immune based therapies is off-target effects that can be deadly. Central tolerance is the process of negative selection that occurs in the bone marrow and thymus to eliminate self-reactive antibodies and TCRs respectively. In silico models are trained with random self-antigen complexes 435 and a loss function 460 to minimize the affinity towards these random proteins while maximizing affinity, or a specific value, of the desired antigen (see FIG. 4 460). For many applications, a high diversity protein complex can be generated nearly instantly while minimizing cross-reactivity 170.

Another embodiment is the option for an exhaustive search for self-reactivity elimination. The previously mentioned negative selection minimization during training may not guarantee a safe level of self-reactivity for all applications especially in the case where peripheral tolerance mechanisms are intentionally blocked, such as certain cancer immunotherapies, any cross-reactivity can be dangerous or deadly. In this case, a user can select an option for an exhaustive search (see FIG. 4 option 165 to select process 175) against self-antigens that can be run to predict the affinity for these self-antigens. In the case of TCRs, self-antigens are generated using a specific MHC/HLA combination either provided 140 or parsed from the uploaded genomic information using standard bioinformatics techniques 100. Additionally, any expressed allelic differences can be parsed from individual genomes 100 in order to produce high diversity proteins. An exhaustive search determines the self-reactivity of generated high diversity protein complexes. High diversity protein complexes are passed back into the generative models 160 refining them to lower self-reactivity. The results are then exhaustively searched for self-reactivity again and passed back into the generative models until there is zero or an acceptable level of self-reactivity 180.

Figure 6:
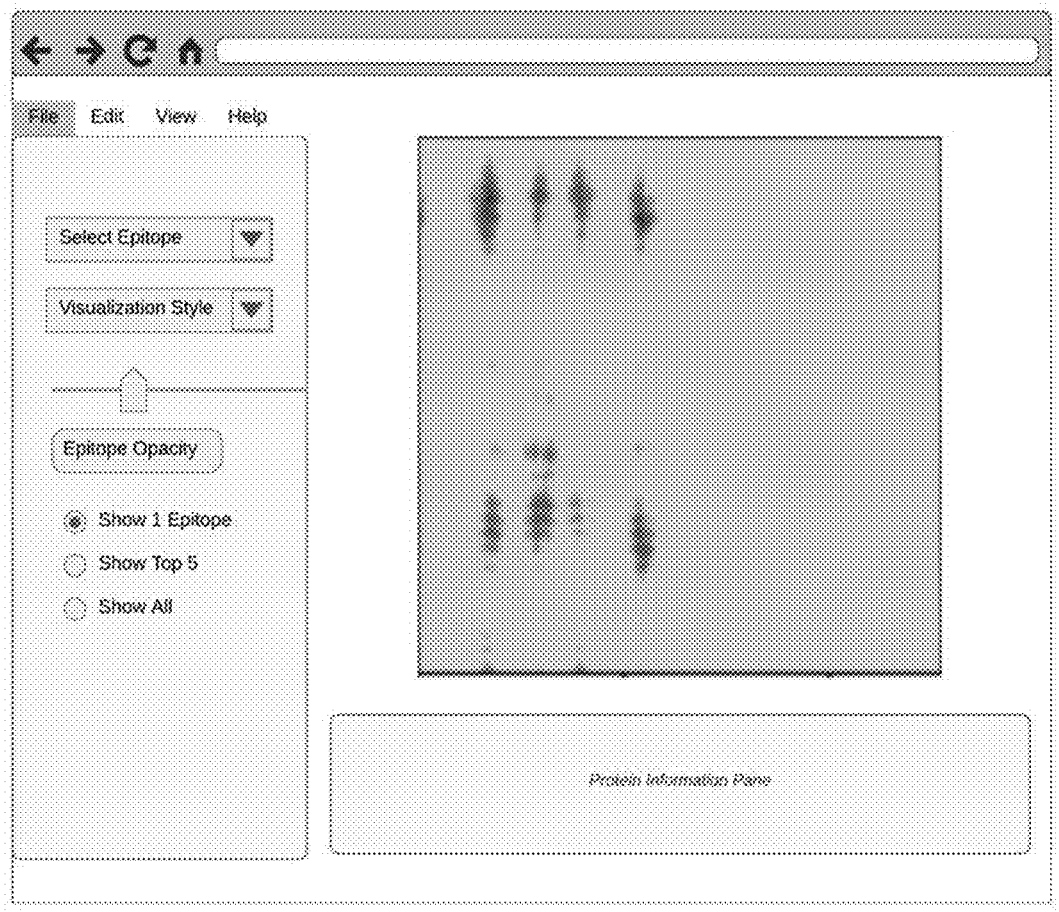
FIG. 6 Mockup of the epitope visualization tool.

One embodiment is an option to sample epitopes from the generative models based on an antigen complex's sequence(s) and use this epitope for generation of antibodies that are specific to that epitope. FIG. 2 gives an overview of this process. A user can upload an antigen complex's sequence 200, select the species of the antibody 205, isotype 210, subtype 215, and allotype 220 (optional). One protein can have multiple epitopes in which an antibody could plausibly bind. Some regions of an antigen complex may be conserved while others may not. A set of epitopes along with probabilities of these epitopes is returned to the user and stored in a database 240 for long term use. A specific generated epitope can then be optionally used in the process as shown in FIG. 1 operation 110. The deep generative models 225 use the same network 400 described previously in FIG. 4 to generate the epitope information 420. First, in the background the antigen complex's sequence(s) are passed to a protein folding generator described previously FIG. 5 500 to generate 3D information including, but not limited to, distance matrices, phi psi angle information, and labeled surface meshes. The structural information along with the conditional information is passed into the trained high diversity protein generator 400 that outputs the desired epitope and other information 420. In order to create an epitope set, the high diversity protein generator 400 is repeatedly sampled with the same conditional information. The probability for an epitope in the set is the fraction of times that epitope was returned with repeated sampling. With the aid of a protein folding generator described previously FIG. 5 500 and a visualization tool, a user can examine these epitopes in order to find the best epitope to use. A mockup of the visualization tool can be seen in FIG. 6. A user has options to select a protein visualization style including, but not limited to, 3D space, as a 2D distance matrix, or a 2D representation of the protein surface mesh. A user also has the option to select a specific epitope from a drop-down list. Available information, such as name, PDB links, basic protein function, etc. are also listed in the visualization tool.

In another embodiment a proprietary database is constructed using in vitro, in vivo, and/or additional in silico results from generated high diversity proteins. The data collected may include, but is not limited to, off target binding, affinity values, self-reactivity, specificity, and tumor cell lysis. The data collected from additional testing is used to validate the results of the deep generative models and to improve the performance of the deep generative models and deep neural network modules.

Figure 3:
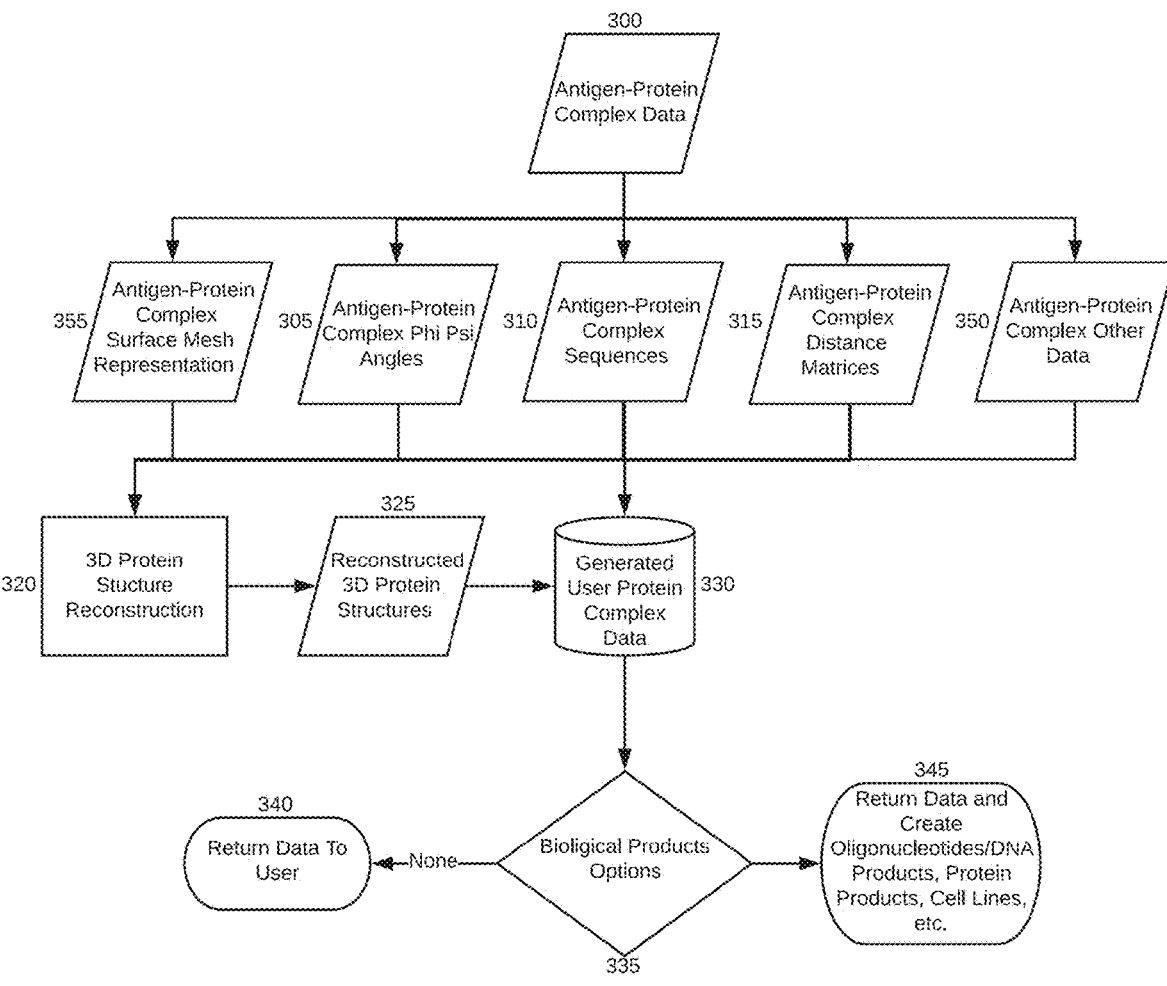
FIG. 3 Flow chart of post generative processing and options.

As seen in FIG. 3, the output produced by the generative models includes, but is not limited to, the high diversity protein-antigen complex's sequences 310, distance matrices 315, phi psi angle information 305, surface mesh representation 355, and if applicable other information such as the epitope and paratope of the high diversity protein-antigen complex 350. Additionally, the information produced is used to generate 3D protein structures of both the protein complex and the antigen complex 320. The 3D structures 325 are recovered in process 320 from 2D distance matrices 315 using multidimensional scaling to extract Cartesian coordinates of amino acid α-carbons. Full atom reconstruction is done by using predicted phi and psi dihedral angles 305 and sequences 310. The 3D data and other high diversity protein-antigen complex data is stored in a database to allow a user to retain the data after it is created 330.

FIG. 3 shows a process of how to rapidly deploy generated data. After a high diversity protein complex is generated 300, the sequences of this high diversity protein complex 310 stored in a database 330 can be directly sent to an oligonucleotide synthesizer or other DNA synthesis technology 345 if a user chooses this option 335. If a user does not select an option for biological products 335 only the high diversity protein-antigen complex data will be returned 340. The produced nucleotides can then be shipped to an end user or the process of creating protein complexes or cell lines can begin using commercially available technology 345.

An illustrative example for this web-based platform is the use during an outbreak of a novel virus. One of the first steps during a novel virus outbreak is to sequence the viral genome. After the genome is sequenced, a user of this web-based platform can upload a likely spike protein of this virus and explore potential epitopes using the interface in FIG. 2 for example. The viral protein sequence is uploaded 200 with the species set to human 205 IgG1 210/215 and no allotype 220. This conditional information is passed into deep generative models 225 (using the same network as 400 and part of the generated data 420). After a set of epitopes is generated with probabilities of occurrence 230 and stored in a database 240, a user can visualize the epitope locations on the 3D protein structure using the visualization tool shown in FIG. 6. The user, using his/her best judgment, such as seeing a conserved region on the spike protein between related viruses, chooses an epitope. A user then uses this epitope for the web interface options in FIG. 1. This user selects one hundred high diversity proteins to return 190, adds the spike protein's sequence(s) 105, and the generated epitope 110. The user then selects human as the species 115, a high affinity 120, minimizes the cross-reactivity by default 125, selects antibody as the type of high diversity protein 130, of IgG1 135/145, and an exhaustive search 165. In the background, the uploaded viral protein sequence is folded using the trained protein folding generator module 500 and output 525 for use as conditional data for the deep generative models 160.

After the conditional 3D information 525 of the viral protein is generated 500, this information and the previously mentioned conditional information from FIG. 1 is passed to the trained high diversity protein generator 400 and an initial antibody set is produced 420. Since an exhaustive search was selected 165, a larger number than the total number to return 190 is generated for the initial set if possible. The first check for generated antibodies is to confirm that the antibodies provided conditional information matches the predictions of the pre-trained modules in 405, such as affinity 445 and species 450. Generated antibodies that pass this first check move onto an exhaustive cross-reactivity search using the trained affinity prediction module 445. The affinity of each antibody in the set is predicted for every protein product in the human genome or a subset of proteins that could interact with antibodies, such as membrane proteins. If antibodies in the set are found to interact with human proteins, the specific antibodies are removed from the set. In this case, after all affinity predictions are complete, no antibodies were found that had zero cross-reactivity. In this situation, the next step is to update the high diversity protein generator 400 for this user to generate a new antibody that does not bind to the found cross-reactive proteins. These cross-reactive proteins are used for cross-reactivity minimization 480. In order to minimize large changes to the high diversity protein generator 400, the antibodies with the smallest amount of cross reactivity are used in place of real antibodies for training 430. The weights of the high diversity protein generator are updated with the losses from the modules of the discriminator 400. The training process continues for several iterations until the affinity minimization set reaches an acceptable threshold. After the training update, a new set of antibodies is generated for the exhaustive search. This time over 100 antibodies have no found cross-reactivity otherwise the process would repeat until antibodies without cross-reactivity were found.

After the antibody set has been refined 180, the data is used to create 3D protein structures 320 from the generated sequences 310, distance matrices 315, angle information 305, and other data 350. The generated data and reconstructed 3D protein data 325 is then stored in a database 330. The user examines the results FIG. 3 330 using visualization such as FIG. 6 and/or other commercially available tools and data. In examining the antibodies, many of them bind at angles that are physically blocked by other areas of an assembled virus. The user does see several antibodies that bind at angles that are not physically blocked on the spike protein by other areas of the virus. The user is satisfied with the subset that is not physically blocked and selects the biological products option to produce these generated antibodies. As part of an agreement with the user, the results of in vitro and in vivo studies of the generated antibodies are added to the proprietary database to further improve the in silico high diversity protein generation process. These antibodies are then shipped to the user for use in testing to facilitate rapid development of monoclonal antibody treatments for this novel virus for use in high risk individuals.

Another illustrative example is using the platform for cancer immunotherapy. A user at a clinic, after genomic analysis of the multiple metastases, finds that an intact antigen presentation system is present, along with a mutated surface protein. First, this user uploads the mutated surface protein 105, along with the patient's genome 100, and selects one antibody to return 190 without manually specifying an epitope 110. After parsing the patient's uploaded genome 100, several allelic variants were discovered including a constitutively expressed point mutation in a protein of hepatocytes that changed a proline to a histidine. The species 115 is automatically parsed from the uploaded genome 100 and the user opts to maximize affinity 120. The cross-reactivity option is hidden from this user 125, since this user is using the platform for therapeutic use. The protein complex type is selected to be antibody 130, the isotype 135 and subtype 145 are then selected. The allotype of the antibody is automatically inferred from the genome 155. The user opts to use an exhaustive search 165. Unlike the previous example no cross-reactive proteins were found and the antibody-antigen complex data is returned to the user 330. The user chooses to immediately start the production of antibodies for the patient 335/345 and when complete, the antibodies are shipped to the user.

Other tumor specific antigens are present and expressed in MHC. This user uploads the patient's genome 100, and the sequences of multiple other tumor specific antigens 105 and selects to have one TCR returned per antigen complex sequence in the set 190. The species 115 is inferred from the uploaded genome. The user selects automatic affinity 120 and protein complex type of TCR. The MHC allelic combination 140 is inferred from the uploaded genome. The user then selects the $\alpha\beta$ chain type 150, and MHC class I 185. The user selects for an exhaustive search 165. In the background the platform automatically creates peptide epitopes that bind to the uploaded MHC allelic variants for use as conditional data 415. After an initial set of TCRs is generated, the set of TCRs is then passed through the exhaustive affinity search. Most TCRs specific to the uploaded tumor specific antigens were found to have no cross-reactivity. One TCR for an epitope of one tumor specific antigen was found to bind strongly to the previously mentioned allelic variant expressed in hepatocytes. If the patient's genome 100 was not uploaded, the patient could have had a potentially fatal immune reaction from one of the generated TCRs. The high diversity protein generator is updated as mentioned in the previous illustrative example. The TCR set, now free of cross-reactivity, is saved to the database 330 for further use along with 3D protein data construction 320. The user selects false for the biological products options and uses the sequence data to create modified CD8+ T-cells collected from the patient at a local university. As part of the user agreement, results and side effects from the patient are returned and added to the proprietary database to improve the results and safety of the in silico high diversity protein generation process.

What is claimed:

1. A system for de novo generation of protein complexes in silico, the system comprising:
   a system processor connected to an input/output interface and a memory via a communications network,
   wherein said processor is programmed with a generative model,
   wherein said generative model is programmed to generate a plurality of high diversity protein complex outputs de novo using a first set of input information, the first set of input information comprising one or more antigen complex conditional information input value,
   wherein said protein complex outputs each have selective affinity and cross-reactivity minimization based on said first set of input information,
   wherein said generative model comprises one or more generative adversarial network (GAN), and
   wherein said generative model is further trained with one or more neural network module with one of the group consisting of: protein data, immune epitope data, antibody affinity data, TCR affinity data, off-target binding data, and combinations thereof;
   a protein folding module configured to assist said generative model to produce three-dimensional (3D) structural data for said protein complex outputs; and
   a discriminator module configured to compare said protein complex outputs with real protein complex data for continuous training of said generative model.

2. The system of claim 1, wherein said protein complex outputs are selected from the group consisting of: antibody outputs, T-cell receptor (TCR) outputs, and combinations thereof.

3. The system of claim 1, wherein said input information is selected from the group consisting of: an antigen complex sequence, species information, isotype information, subtype information, allotype information, affinity information, cross-reactivity conditions, and combinations thereof.

4. The system of claim 1, wherein said protein complex outputs comprise protein complex distance matrices, angle information, and surface mesh representations.

5. The system of claim 1, wherein said protein complex outputs comprise protein complex affinity information, epitope information, and paratope information.

6. The system of claim 1, further comprising:

an affinity module configured to predict affinity between said protein complex outputs and an antigen to be targeted to update generated affinity output to match expected affinity and minimize cross-reactivity of said protein complex outputs.

7. The system of claim 1, wherein:

said system is further configured to send said protein complex outputs to an oligonucleotide synthesizer to begin creation of proteins or cell lines according to said protein complex outputs.

8. The system of claim 1, wherein said input/output interface is accessible to a user via a web-based platform.

9. A method of generating high diversity protein complexes in silico, the method comprising:

providing a system processor connected to an input/output interface and a memory via a communications network, wherein said processor is programmed with a generative model, and wherein said generative model is trained using one or more neural network module with protein data, immune epitope data, antibody affinity data, TCR affinity data, and off-target binding data and programmed for generation of high diversity protein complexes de novo to target an antigen of using a first set of input information, wherein the first set input information comprises one or more antigen complex conditional information input value;

providing a protein folding module configured to assist said generative model to produce three-dimensional (3D) structural data for said protein complex outputs;

providing a discriminator module configured to compare said protein complex outputs with real protein complex data for continuous training of said generative model;

inputting the first set of input information into said system processor; and generating a plurality of high diversity protein complex outputs de novo with selective affinity and cross-reactivity minimization based on said first set of input information.

10. The method of claim 9, wherein said first set of input information is selected from the group consisting of: an antigen complex sequence, species information, isotype information, subtype information, allotype information, affinity information, cross-reactivity conditions, and combinations thereof.

11. The method of claim 9, wherein said protein complex outputs comprise protein complex distance matrices, angle information, surface mesh representations, affinity, epitope, and paratope information.

12. The method of claim 9, further comprising:

sending said protein complex outputs directly to an oligonucleotide synthesizer:

said oligonucleotide synthesizer creating proteins or cell lines according to said protein complex outputs; and testing for safety of said protein complex outputs in vitro.

13. The method of claim 9, further comprising:

performing an exhaustive search for self-reactivity of said protein complex outputs.

14. The method of claim 9, further comprising:

performing an exhaustive search for cross-reactivity with all proteins for a particular species.

15. The method of claim 9, wherein said first set of input information comprises tumor specific antigen complex conditional information unique to an individual.

16. The method of claim 9, further comprising:

further training said generative model with said protein complex outputs to further minimize cross-reactivity of additional protein complex outputs.

17. A system for de novo generation of protein complexes in silico, the system comprising:

a system processor connected to an input/output interface and a memory via a communications network:

wherein said processor is programmed with a generative model:

wherein said generative model is programmed to generate a plurality of high diversity protein complex outputs de novo using a first set of input information, the first set of input information comprising one or more antigen complex conditional information input value;

wherein said input information is selected from the group consisting of: an antigen complex sequence, species information, isotype information, subtype information, allotype information, affinity information, cross-reactivity conditions, and combinations thereof;

wherein said generative model comprises one or more generative adversarial network (GAN);

wherein said generative model is further trained with one or more neural network module with one of the group consisting of: protein data, immune epitope data, antibody affinity data, TCR affinity data, off-target binding data, and combinations thereof;

a protein folding module configured to assist said generative model to produce three-dimensional (3D) structural data for said protein complex outputs;

an affinity module configured to predict affinity between said protein complex outputs and an antigen to be targeted to update generated affinity output to match expected affinity and minimize cross-reactivity of said protein complex outputs;

wherein said protein complex outputs are selected from the group consisting of: antibody outputs, T-cell receptor (TCR) outputs, and combinations thereof;

wherein said protein complex outputs each have selective affinity and cross-reactivity minimization based on said first set of input information; and wherein said protein complex outputs comprise protein complex affinity information, epitope information, and paratope information.

* * * * *